(12) United States Patent
Schlund et al.

(10) Patent No.: US 11,759,102 B2
(45) Date of Patent: *Sep. 19, 2023

(54) DEVICE AND METHODS FOR MONITORING A VISUAL FIELD PROGRESSION OF A USER

(71) Applicant: Sensimed SA, Etagnières (CH)

(72) Inventors: Mario Schlund, Ecublens (CH); Thierry Varidel, Ecublens (CH); Raphael Fritschi, Lausanne (CH); Carlos Gustavo De Moraes, New York, NY (US)

(73) Assignee: Sensimed SA, Etagnières (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/824,209

(22) Filed: May 25, 2022

(65) Prior Publication Data

US 2022/0304567 A1 Sep. 29, 2022

Related U.S. Application Data

(63) Continuation of application No. 16/622,598, filed as application No. PCT/EP2017/064628 on Jun. 14, 2017, now Pat. No. 11,369,262.

(51) Int. Cl.
*A61B 3/00* (2006.01)
*A61B 3/024* (2006.01)
(Continued)

(52) U.S. Cl.
CPC ............ *A61B 3/0025* (2013.01); *A61B 3/024* (2013.01); *A61B 3/107* (2013.01); *A61B 3/16* (2013.01)

(58) Field of Classification Search
CPC ....... A61B 3/0025; A61B 3/024; A61B 3/107; A61B 3/16; A61B 5/0002; A61B 5/6821; G16H 50/30
(Continued)

(56) References Cited

U.S. PATENT DOCUMENTS

| 11,369,262 B2 * | 6/2022 | Schlund ............... A61B 3/0025 |
| 2003/0049602 A1 * | 3/2003 | Schaffer ............. G01N 33/5058 435/5 |

(Continued)

FOREIGN PATENT DOCUMENTS

CN 101766473 A 7/2010

OTHER PUBLICATIONS

International Search Report & Written Opinion issued for PCT/EP2017/064628; dated Apr. 11, 2018.

*Primary Examiner* — Mohammed A Hasan

(74) *Attorney, Agent, or Firm* — Dinsmore & Shohl LLP; Weston R. Gould

(57) ABSTRACT

This disclosure provides a method for determining the likelihood of being at or beyond a certain rate and/or risk of visual field progression (VFP) of a user, that may include measuring ocular biomechanical properties (OBP) through a continuous-wear sensor placed on or implanted in the eye; recording the user's ocular biomechanical properties in the form of at least one OBP time series plot in a recorder, a processing step wherein at least one of a plurality of OBP parameters are extracted from the recorded OBP time series plot; a calculation step wherein the at least one of a plurality of OBP parameters are associated to VFP, and a determining step wherein one determines whether the visual field progression is at or beyond a certain VFP threshold and/or the probability that the said visual field progression is comprised within a specific range.

16 Claims, 4 Drawing Sheets

(51) Int. Cl.
*A61B 3/107* (2006.01)
*A61B 3/16* (2006.01)

(58) Field of Classification Search
USPC .......................................................... 351/206
See application file for complete search history.

(56) References Cited

U.S. PATENT DOCUMENTS

| | | | |
|---|---|---|---|
| 2003/0099944 A1* | 5/2003 | Schaffer | G01N 33/5008 |
| | | | 435/5 |
| 2009/0076367 A1 | 3/2009 | Sit et al. | |
| 2011/0091459 A1* | 4/2011 | Gant | A61K 31/4353 |
| | | | 514/363 |
| 2014/0016097 A1* | 1/2014 | Leonardi | A61B 3/0041 |
| | | | 351/219 |
| 2015/0019361 A1 | 1/2015 | Denton et al. | |
| 2018/0014724 A1* | 1/2018 | Wroblewski | G16H 10/60 |

* cited by examiner

DEVICE AND METHODS FOR MONITORING A VISUAL FIELD PROGRESSION OF A USER

CROSS REFERENCE TO RELATED APPLICATIONS

This application is a continuation of U.S. patent application Ser. No. 16/622,598 filed Dec. 13, 2019, which is a U.S. National Stage of PCT/EP2017/064628 filed Jun. 14, 2017, the entire contents of each of which are incorporated herein by reference.

TECHNICAL FIELD

The present invention relates to a device and methods for monitoring ocular biomechanical properties (OBP) and/or for detecting and/or diagnosing and/or surveying ophthalmic diseases. The present invention relates in particular to a system and a method comprising a device that can be placed on the eye of a user in order to monitor one or more OBP including for example the intraocular volume (IOV) and the intraocular pressure (IOP), and changes thereof over an extended period of time, and adapted to use these OBP for predicting a visual field progression of the monitored user.

BACKGROUND OF THE ART

Glaucoma is a heterogeneous group of progressive optic neuropathies, characterized by loss of retinal ganglion cells (RGC), leading ultimately to loss of vision and subsequent irreversible blindness. Early diagnosis and effective management is key, as the disease is treatable and its progression can be slowed or halted, while glaucomatous visual impairment is irreversible. The disease is a slowly progressing condition in most individuals. Some may remain asymptomatic for years and progress slowly. However, others experience rapid disease progression, putting the individual at risk of visual impairment or blindness.

Progression of glaucoma represents worsening of the disease, i.e. additional visual field loss associated with the death of optic neurons. Clinically, progression is classified as functional when referring to visual field progression (VFP), and structural when referring to changes in the retinal nerve fiber layer (RNFL). Both, functional and structural changes can be assessed over time to understand the rate of change and hence the progression of the disease.

Functional progression is related to the user's actual visual function as assessed by visual field (VF) testing. Sequential VF testing data from each glaucoma subject is at the basis of the estimation of the individual's glaucomatous VFP in clinical practice. As such, the VFP is assessed using discrete measurements over months and years to estimate the progression and the speed of progression (in dB/year) of a user knowing that once VF shows progression the impairment is irreversible.

One way to overcome the delay in VFP measurement, hence avoid the irreversible damage, is to estimate the likelihood of VFP based on the IOP, as being the only modifiable risk factor for the development and progression of glaucoma. However, the role of IOP in the disease is not fully understood; especially as individual susceptibility to IOP may differ, explaining why a significant number of users with normal IOP could develop glaucoma or experience VFP, while others with elevated IOP show no sign of the disease or little VFP. This constitutes a limitation in the use of IOP as estimator of likelihood for VFP that can be mitigated sequencing the IOP discrete measurements for a longer period.

A further technique for estimating the VFP risk is called Ocular Response Analyzer (ORA). This technique measures the delay in tissue movement in and out caused by the cornea's viscoelastic resistance, as an indicator of biomechanical condition. In this technique, a variable pressure is rapidly applied to the eye through air pulses and an electrooptical system takes data samples of the corneal hysteresis which is the difference measured between pressures recorded at two moments of applanation. This technique also gives information regarding Corneal Compensated IOP, Corneal Resistance Factor and Goldmann Correlated IOP. This technique is however mainly used as a research tool only.

Devices for measuring the IOP over a period of time are known in the art. These devices typically comprise a pressure sensor for continuously measuring the IOP, which is embedded for example into a contact lens that is placed in a non-invasive way on the user's eye, or into a support that is implanted into the user's eye. These devices further comprise a receiving unit and a telemetry system for acquiring IOP data from the sensor at given intervals over a period of time. The IOP values measured and recorded are for example averaged and/or filtered, if needed, and then interpreted by physicians in order to detect elevations of intraocular pressure as additional risk factors that could lead to VFP, which conducts to a gradual loss of vision.

The systems described in the prior art are for example designed to measure a few IOP values per second during a few seconds and perform this measurement cycle every few minutes over a certain period of time, usually up to 24 hours, in order to obtain the circadian or nycthemeral profiles of the IOP.

However, adequate 24-hour measurement is time consuming, expensive and impractical for individual users and for frequent use in clinical practice.

It is therefore an aim of the present invention to provide a system and a method which address these problems and which can, with a 24-hour recording of an OBP-related profile, provide a signature that determines the likelihood of being at or beyond a certain rate and/or risk of VFP at the time of monitoring.

A further object of the invention is to provide a system and a method comprising a real-time measurement of OBP, including for example, but not exclusively, the IOP profile, eye blink and/or rapid eye motion, with a high resolution.

Recently, 24-hour OBP estimation has been possible using devices that provide near-continuous measurements through invasive or minimally-invasive techniques. One such device is the Contact Lens Sensor (CLS) system that records patterns and profiles of changes of ocular dimensions related to IOP. The inbuilt sensor captures spontaneous circumferential changes at the corneo-scleral limbus that occur due to ocular pressure and volume changes. The mean 24-hour pattern of the CLS output signals has been correlated with the mean 24-hour tonometric curve.

Recently, we discovered that certain OBP derived from CLS signals were associated to users experiencing VFP. In addition, this signature obtained during a one-day session was a better predictor of VFP than IOP measurements taken multiple times over years. It is therefore another aim of the present invention to provide systems and methods of computing and analyzing the recorded data in order to diagnose ophthalmic diseases such as for example, glaucoma, and/or to estimate the likelihood of VFP in order to increase the prediction provided by the IOP before the visual damage occurs.

SUMMARY OF THE INVENTION

These aims and other advantages are achieved by a system and methods according to the respective independent claims.

Following terms are being used hereafter

Ocular biomechanical properties (OBP), such as intraocular pressure (IOP), intraocular volume (IOV), corneal rigidity, corneal thickness, geometrical dimensions and/or temperature of the eye and more generally any ocular property even non-biomechanical like a specific concentration.

Ocular biomechanical properties (OBP) parameters, derived from OBP data, such as amplitude, minimum, maximum, standard-deviation, number of peaks, slopes, fitted cosinor curve of a 24-hour OBP profile, number of large peaks, mean peak ratio, amplitude of the cosine curve, wake-to-sleep slope, variability from the mean and area under the curve, or a combination thereof.

Continuous-wear sensor: a sensor being continuously worn on or implanted in the eye.

Visual field progression (VFP): speed of the visual field degradation, most often expressed as the slope of mean defect over time.

User: the term user here is designating both, a glaucoma patient or a healthy subject, who wears the sensor.

A first aspect of the invention is a method for determining the likelihood of being at or beyond a certain visual field progression (VFP) of a user, comprising the following steps:

a measuring step comprising measuring ocular biomechanical properties (OBP) through a continuous-wear sensor placed on or implanted in the eye, with said measurement comprising repeated data capture at regular time intervals;

a recording step comprising recording the user's ocular biomechanical properties in the form of at least one OBP time series plot in a recorder, a processing step wherein at least one of a plurality of OBP parameters are extracted from the recorded OBP time series plot;

a calculation step wherein the at least one of a plurality of OBP parameters are associated to VFP, and a determining step wherein one determines whether the visual field progression is at or beyond a certain VFP threshold and/or the probability that the said visual field progression is comprised within a specific range so as to determine the likelihood of being at or beyond a certain VFP.

Advantageously, in this manner VFP can be estimated with a single measurement session lasting for example 24-hours, combined with additional metadata, instead of collecting a sequence of individual measurements, such as visual fields, over the course of several months or years.

According to a preferred embodiment of the present invention, during the processing step 55 OBP parameters are extracted, and are then combined through linear combination to provide 4 final parameters.

Advantageously, the extracted OBP parameters are at least one taken from the group comprising amplitude, minimum, maximum, standard-deviation, number of peaks, slopes, fitted cosinor curve of a 24-hour OBP profile, number of large peaks, mean peak ratio, amplitude of the cosine curve, wake-to-sleep slope, variability from the mean and area under the curve, or a combination thereof. In this manner, the raw OBP measurement can be synthetized into a reduced set of parameters.

According to a preferred embodiment of the present invention, in the calculation step, the extracted OBP parameters are combined with additional user metadata.

Preferably, the extracted OBP parameters and additional user metadata are combined through a logistic model. Thanks to this, and on top of VFP assessment, the meaning of the OBP parameters can be conveniently explained to the healthcare professional.

Advantageously, the additional user metadata are taken from the group comprising latest IOP data, age, a number of medications taken during past 5 years, latest visual field mean defect data, such as to have the best possible description of current user disease status.

According to a preferred embodiment of the present invention, the continuous-wear sensor is a wireless Contact Lens Sensor such as the SENSIMED Triggerfish.

Advantageously, the method further comprises an OBP data downloading step comprising transferring the OBP data from the recorder to a computer. Thanks to this the healthcare professional can store and review the recorded OBP data on their usual computer environment.

Preferably, the downloading step consists in a wireless data transfer. In this manner, the number of cables is reduced.

Preferably, the method further comprises a cleaning step prior to the processing step and adapted to clean the OBP data by deleting the bad quality measured data. Thanks to this, erroneous VFP assessments due to bad OBP data quality can be reduced or avoided.

Advantageously, the method further comprises a result communicating step after the calculation step, adapted to send a signal to a receiver, said signal indicating the likelihood of being at or beyond a certain VFP.

According to a preferred embodiment of the present invention, the method is a computer-implemented method. This embodiment is particularly adapted for implementation of complex, CPU-intensive algorithms.

A second aspect of the invention relates to a system for predicting VFP in a user, based on OBP data measured by a wireless sensor by carrying out the process of the first aspect of the invention, the system comprising:

a measuring step comprising measuring ocular biomechanical properties (OBP) through a continuous-wear sensor placed on or implanted in the eye, with said measurement comprising repeated data capture at regular time intervals;

a recording step comprising recording the user's ocular biomechanical properties in the form of at least one OBP time series plot in a recorder, a processing step wherein at least one of a plurality of OBP parameters are extracted from the recorded OBP time series plot;

a calculation step wherein the at least one of a plurality of OBP parameters are associated to VFP, and a determining step wherein one determines whether the visual field progression is at or beyond a certain VFP threshold and/or the probability that the said visual field progression is comprised within a specific range so as to determine the likelihood of being at or beyond a certain VFP.

The particular advantages of this system of the invention being similar to the ones of the method of the first aspect of the invention, they will not be repeated here.

For the first time, thanks to the present invention, the prediction of VFP is not based on the measurements of a time sequence of historic visual field data (e.g. multiple measurements at 9/12-month interval), but is calculated from one single measurement of visual field combined with some meta data and parameters extracted from a device-related 24-hour signal, which are an expression of the OBP.

The above-mentioned data then provides the healthcare professional with a tool that computes the likelihood of being at or beyond a certain visual field progression (VFP).

BRIEF DESCRIPTION OF THE DRAWINGS

Further particular advantages and features of the invention will become more apparent from the following non-limitative description of at least one embodiment of the invention which will refer to the accompanying drawings, wherein FIG. 1 schematically represents a preferred embodiment of the method of the present invention.

DETAILED DESCRIPTION OF THE INVENTION

The present detailed description is intended to illustrate the invention in a non-limitative manner since any feature of an embodiment may be combined with any other feature of a different embodiment in an advantageous manner.

In embodiments, the present invention relates to a device, a system and methods for measuring and/or monitoring one or more ocular biomechanical properties (OBP) in order for example to determine the response of an eye of a user to various events and/or situations including for example, but not exclusively, an eye blink stimulation, the pulsation of IOV and/or IOP, the rapid eye motion during a period of sleep, the use of drugs or medication, physical activity of the user, etc., using a continuously worn system capable of measuring at least one OBP, including for example, but not exclusively, intraocular pressure, corneal curvature and/or micro-displacement of the eye, with a frequency at least twice as high as the frequency of the changes of the at least one parameter to be measured, for example at least 10 Hz, over an extended period of time. In embodiments, the present invention further describes a system comprising a computer having algorithms, or a computer program thereon able to display, analyze and process the measured data and give for example essential information on the ophthalmic condition of the eye when the computer program is run on the computer.

Figure 1:
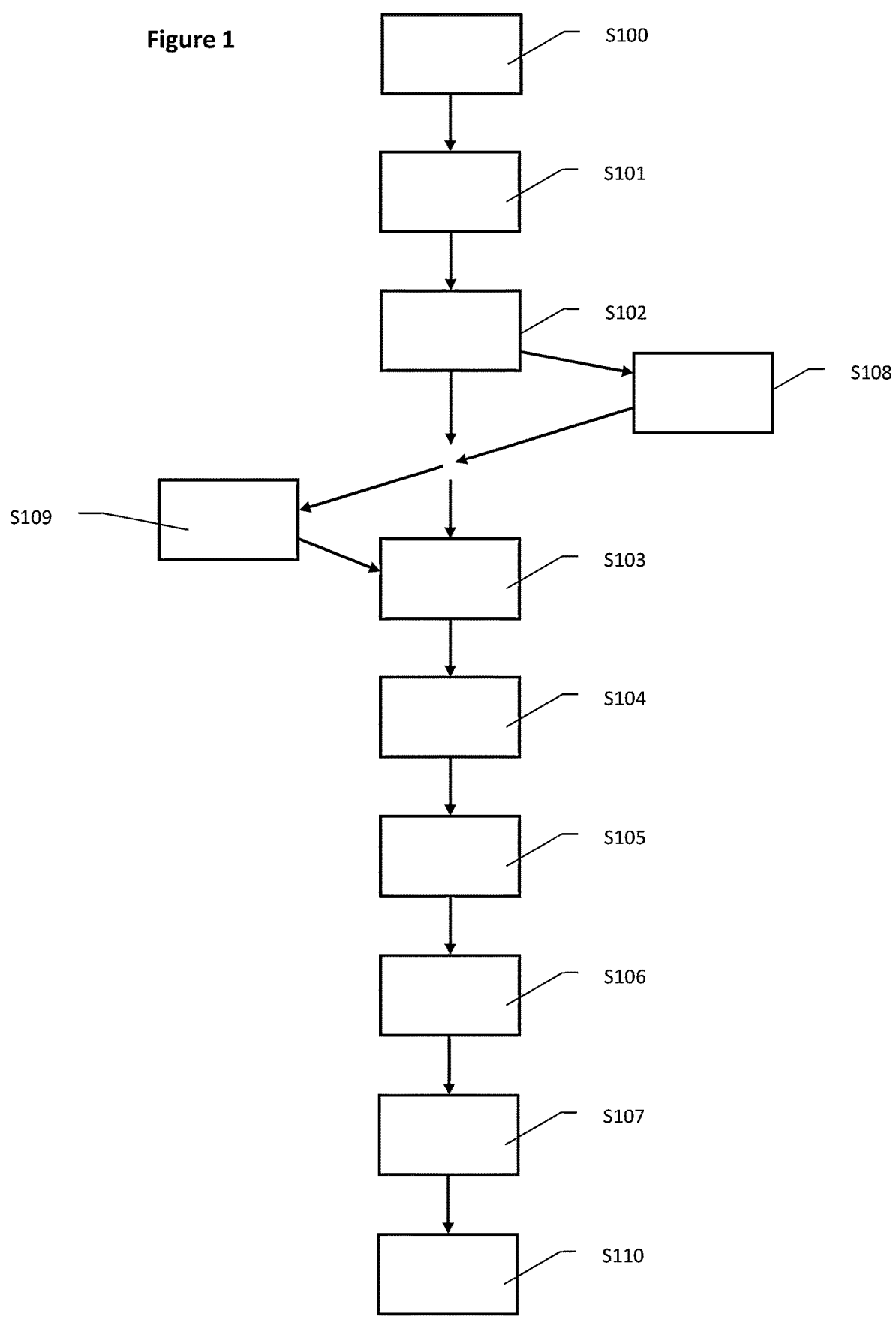

FIG. 1 represents a first aspect of the invention which is a method for predicting visual field progression (VFP) in a user and/or for determining the likelihood of being at or beyond a certain rate and/or risk of visual field progression of a user.

The method of the invention which is preferably a computer-implemented method, comprises a measuring step S101 comprising measuring ocular biomechanical properties (OBP) during through a continuous-wear sensor, preferably a wireless Contact Lens Sensor, placed on or implanted in the eye, with said measurement comprising repeated data capture at regular time intervals. Preferably, the predetermined measuring frequency is equal to or higher than twice the frequency of the variations of the at least one OBP to be monitored. The predetermined frequency thus for example depends on the finality of the monitoring. The predetermined frequency for example depends on the known or supposed frequency of an event inducing a variation of the measured at least one OBP.

In preferred embodiments, the predetermined frequency is chosen to allow for a precise and detailed representation of the variations of the at least one OBP. The predetermined measuring frequency is thus for example in the range of 10 to 20 Hz in order to allow a precise representation of the variation of the at least one OBP in a short period of time, for example the variation of the pulsation of IOV and/or IOP.

The at least one OBP is for example measured at the predetermined frequency over an extended period of time, for example seconds, minutes or hours depending for example on the variations of the at least one OBP that need to be analyzed and/or on the diagnosis that needs to be made. In embodiments, the at least one OBP is measured at the predetermined frequency for limited periods of time, for example some seconds or some minutes, wherein the limited measuring periods are repeated for example at regular intervals or upon triggering, for example upon occurrence of a particular event.

The method of the invention thus allows a precise monitoring of the variations of the at least one OBP over extended periods of time, including at night, while the user is asleep.

The measuring step is followed by a recording step S102 comprising recording the user's OBP in the form of at least one OBP time series plot in a recorder.

The processing step S103 is carried out wherein at least one of a plurality of OBP parameters are extracted from the recorded OBP time series plot, then the calculation step S104 is carried out wherein the at least one of a plurality of OBP parameters are associated to a rate and/or risk of VFP, and finally a determining step S105 is executed wherein one determines whether the visual field progression is at or beyond a certain VFP threshold and/or the probability that the said visual field progression is comprised within a specific range which preferably determines that the visual field progression is fast if the speed of progression is −1.0 dB/year or less, preferably 0 dB/year or less. According to a preferred embodiment of the present invention, the processing step S103 extracts 55 parameters which are then again combined through linear combination to provide 4 final parameters. These extracted OBP parameters can be at least one taken from the group comprising amplitude, minimum, maximum, standard-deviation, number of peaks, slopes, fitted cosinor curve of a 24-hour OBP profile, number of large peaks, mean peak ratio, amplitude of the cosine curve, wake-to-sleep slope, variability from the mean and area under the curve, or a combination thereof.

In order to clearly illustrate the determining step, one considers three examples of the determining step:

According to a first example, the determining step determines the probability the patient has a VFP smaller/larger than −1.0 dB/year. In such an example, if the determining step determines, thanks to the processing and calculating steps, that the probability is 65% to have a VFP smaller than −1.0 dB/year, then the method displays that the user is a fast progressor, i.e. the VFP is deteriorating;

According to a second example, the determining step does not determine whether the visual field progression is at or beyond a certain VFP threshold but determines the VFP and in addition determines the probability that the VFP is within a specific range (confidence interval or maximal standard deviation). In such an example, the determining step first determines, thanks to the processing and calculating steps, that the VFP is −0.82 dB/year for example, and then determines that there is a probability of 95% that it is within a confidence interval of −0.67 to −0.94 dB/year.

According to a third example, the determining step could combine the above two examples and first determine the VFP and the probability that the VFP is within a specific range (confidence interval or maximal standard deviation) and based on that then determine whether the visual field progression is at or beyond a certain VFP threshold. In such an example, the determining step first determines, thanks to the processing and calculating steps, that the VFP is −0.82 dB/year for example, and then determines that there is a probability of 95% that it is within a confidence interval of −0.67 to −0.94 dB/year and finally based on this determines that there is a 98% probability of having a VFP greater than −1.0 dB/year such that the user is a slow progressor.

More particularly, in order to calculate the relationship between OBP data over 24 hours and rates of visual field mean deviation change or VFP during the period, users undergo 24-hour monitoring. The individual OBP data are smoothed preferably using a locally weighted scatterplot smoothing transform. A peak is defined as a local maximum point in the smoothed OBP signal function. The calculation of the number of peaks is as follows: each trough is considered as the start of a peak. The increase in OBP signal value from the preceding trough to the local maximum is termed the height. The time elapsed from the trough to the local maximum is also known as time-to-peak. The following parameters are used:

Number of large peaks (peaks with height of 90 mV eq or more). This distinction differentiates between peaks that may be very small and frequent, but with little clinical interpretation, and those of greater magnitude that are less likely to be the result of artefacts.

Mean peak ratio (mean peak height to time-to-peak). This parameter considers not only the magnitude of the peak, but also how fast it occurred. A high mean peak ratio suggests peaks with shorter latency that could be more detrimental in glaucoma.

Wake-to-sleep slope (slope from OBP signal modelled by linear regression from 1 hour before to 1 hour after the time the subject went to sleep). A high wake-to-sleep slope suggests that the physiologic increase in signal that occurs at night had high magnitude and had shorter latency, which also could be detrimental in glaucoma.

Amplitude of the cosine curve. This parameter is based on the cosine model fitted to the OBP data using the following equation:

$$y(t) = b_0 + b_1 \cdot \cos\left[\left(\frac{2\pi}{24}\right)t\right] + b_2 \cdot \sin\left[\left(\frac{2\pi}{24}\right)t\right]$$

where y is the observed signal at time t, and $b_0$, $b_1$, and $b_2$ are regression coefficients, estimated from the data. The amplitude is the difference between the maximum and minimum values of the cosine-fit curve divided by 2. This is an overall estimate of the magnitude of signal oscillation during the measured period.

Variability from the mean. This parameter is calculated as OBP signal variability around the mean value of all raw measurements in the respective period:

$$\frac{1}{n-1}\sum_{i=1}^{n}|OBP_{Oi} - OBP_M|$$

where n is the number of OBP measurements over the recording period, $OBP_{Oi}$ is the observed OBP signal, and $OBP_M$ is the mean of OBP signal over the recording period. This parameter reflects the amount of fluctuation of OBP signal during the tested period.

Area under the curve. This parameter is calculated using the smoothed OBP data. Where the smoothed data are standardized such that the value at the beginning of the period is 0. The area is calculated as the sum of areas between the smoothed profile and the reference line at y=0, where the area under the reference line is considered to be negative, all divided by the duration of the period (i.e., time). This parameter reflects the magnitude of OBP signals and the duration at which they remain above a reference line.

For each parameter, we obtain values representative of the period where users are asleep or awake.

Then according to a preferred embodiment of the present invention, in the calculation step S104, the extracted OBP parameters are combined with additional user metadata through a logistic model, where the additional user metadata are taken from the group comprising latest IOP data, age, a number of medications taken during past 5 years, latest visual field mean defect.

The processing and calculation steps can be done either in the recorder if the processing unit is embedded in it or the method further comprises an OBP data downloading step S106 comprising transferring, preferably wireless, the OBP data from the recorder to a computer which comprises the processing unit for carrying out the said steps. Additionally, it must be considered that the method may further comprise a cleaning step S107 prior to the processing step S103 and adapted to clean the OBP data by deleting the bad quality measured data. By bad quality, one means inconsistent or clearly erroneous data.

Finally, the method further comprises a result communicating step S108 after the determining step S105, adapted to send a signal to a receiver, said signal indicating the likelihood of being at or beyond a certain VFP, i.e. a certain rate and/or risk of VFP.

A second aspect of the invention relates to a system for predicting VFP in a user, based on IOV and/or IOP changes measured by a wireless OBP sensor carrying out the process of the first aspect of the invention, the system comprising a continuous-wear sensor placed on or implanted in the eye adapted to measure ocular biomechanical properties (OBP) during preferably 24 hours with repeated data capture at regular time intervals; a recorder adapted to record the user's OBP in the form of at least one OBP time series plot, a processing unit for extracting at least one of a plurality of OBP parameters from the recorded OBP time series plot; a calculation unit for associating the at least one of a plurality of OBP parameters to a rate and/or risk of VFP, and a determining unit for determining whether the visual field progression is at or beyond a certain VFP threshold and/or the probability that the said visual field progression is comprised within a specific range so as to determine the likelihood of being at or beyond a certain rate and/or risk of VFP.

Figure 2:
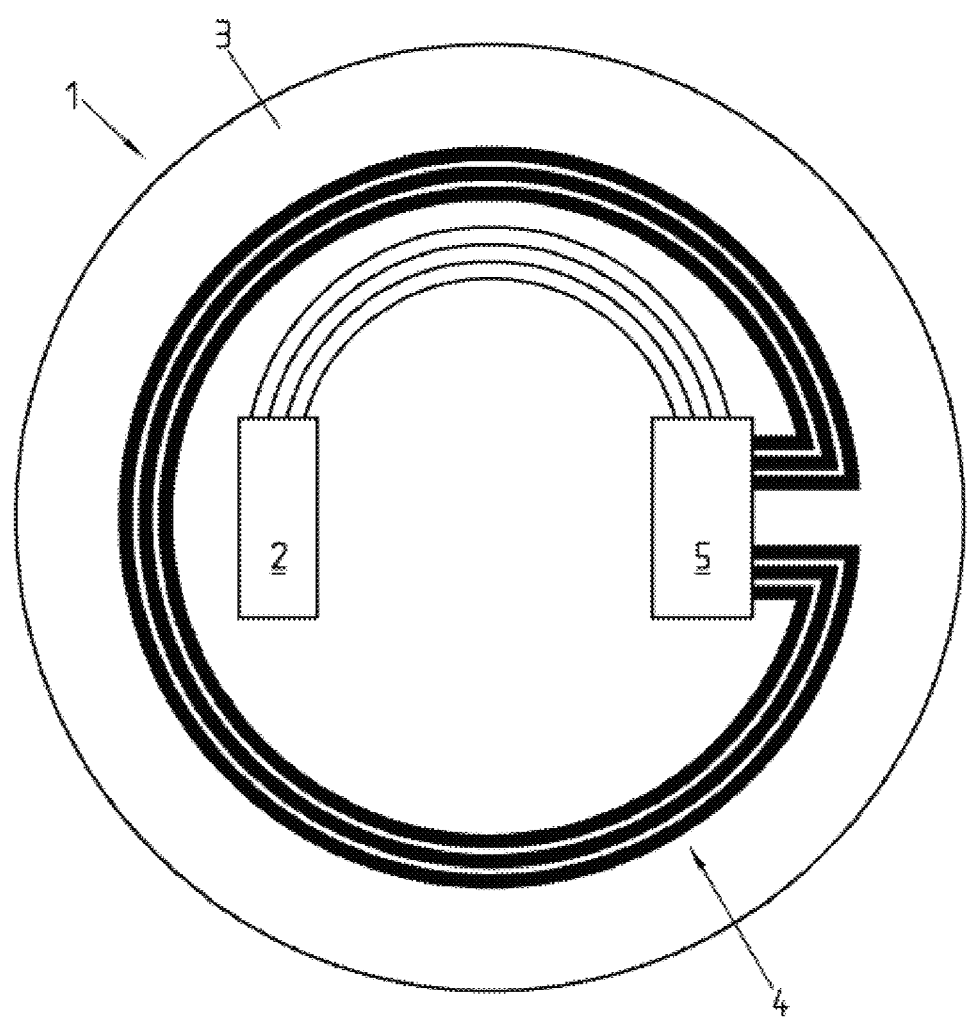
FIG. 2 schematically represents a preferred embodiment of an OBP sensor of the present invention.

More particularly, FIG. 2 schematically illustrates an example of a device 1 for measuring at least one ocular biomechanical property (OBP) over a period of time according to embodiments of the invention. The device 1 for example comprises at least one sensor 2 adapted for measuring an OBP, for example IOV and/or IOP changes. The sensor 2 is attached, preferably fixedly attached, to a support 3. The support 3 is adapted for placing the sensor 2 in direct or indirect contact with the eye of a user in order to allow the sensor 2 measuring the corresponding parameter. In the illustrated embodiment, the support 3 is a contact lens, for example a soft contact lens, and the sensor 2 is for example embedded in the contact lens and positioned such that it is in direct or indirect contact with the surface of the eye when the device 1 is worn by a user like a conventional contact lens.

In other embodiments, the device may be an implantable device that can be implanted into the eye for measuring the at least one OBP, the support being thus adapted for being implanted into the eye.

The sensor 2 is of any type adapted for measuring the at least one OBP. In the illustrated example, the sensor 2 is for example a pressure sensor in the form of a MEMS (Micro Electro Mechanical System), for example a piezoresistive or piezoelectric pressure sensor with a diaphragm and a pressure cavity that create a variable resistance or induced electrical charges for detecting strain due to pressure applied on the diaphragm. Other types of sensors, for example, but not exclusively, other types of pressure sensors, are however possible within the frame of the invention. In embodiments, the sensor is for example a strain sensor using at least one active strain gage and at least one passive strain gage embedded into a support in the form of a contact lens, preferably a soft contact lens, which allows achieving a precise and accurate measurement of IOV and/or IOP changes.

In the illustrated embodiment, the device further comprises a microcontroller 5 and communication means 4, for example an antenna for allowing wireless communication from and/or to the device 1. The microcontroller 5 for example powers the sensor 2, reads measurement data from the sensor 2 that correspond to the value of the at least one measured parameter, optionally at least temporarily stores measurement data and/or sends measurement data over the communication means 4, for example wirelessly sends measurement data over the antenna, to an external device. In other embodiments, the communication means comprises wired communication means. The communication means 4 and the microcontroller 5 are preferably fixedly attached to the support 3, for example embedded in the support 3.

Figure 3:
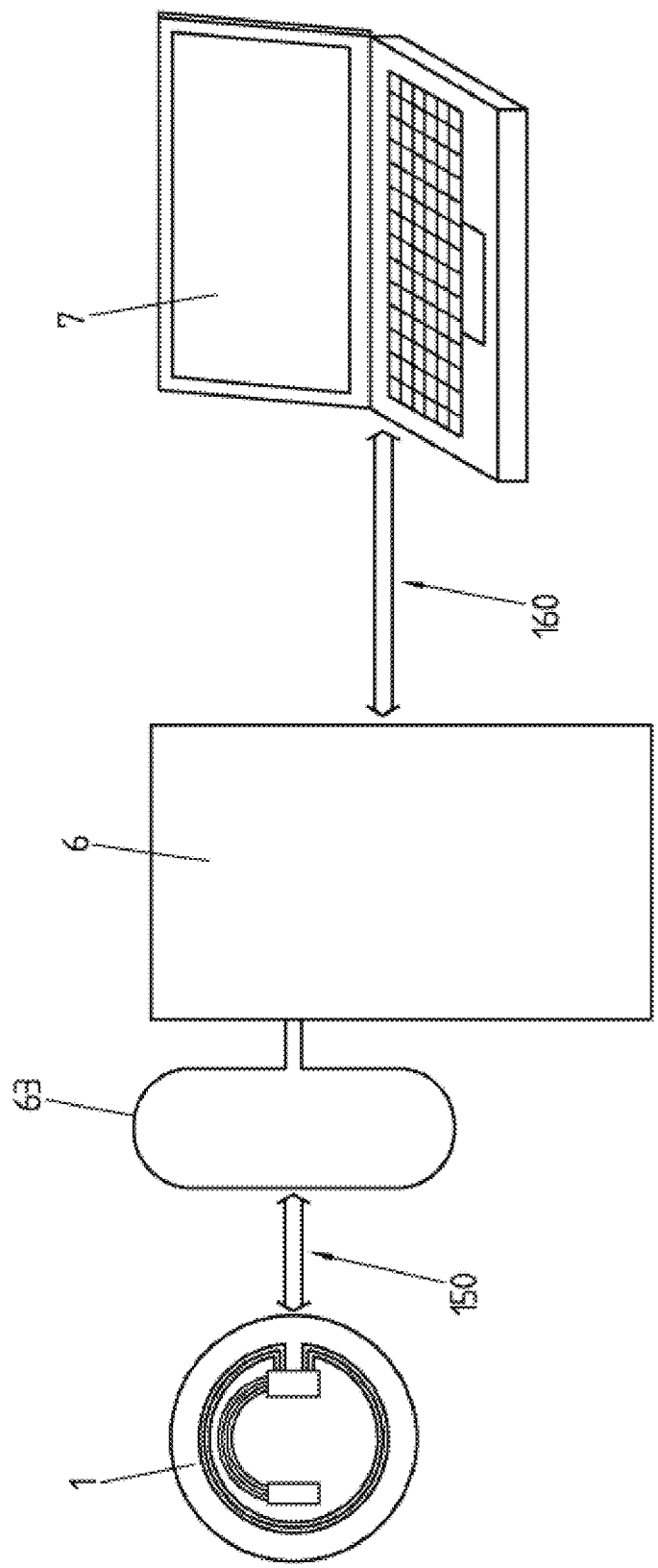
FIG. 3 schematically represents a preferred embodiment of a system of the present invention.

FIG. 3 schematically illustrates an example of a system for monitoring at least one ocular biomechanical property (OBP) and/or for detecting and/or diagnosing ophthalmic diseases, according to embodiments of the invention.

The system for example comprises a measuring device 1 as described above in relation with FIG. 2, for example in the form of a soft contact lens with an OBP sensor, a portable recording device 6 for communicating with the measuring device 1 and/or storing the collected information during the monitoring time periods, and a computing device 7, for example a computer, for storing, analyzing, computing and/or displaying the data collected and stored by the portable communication device 6.

The portable recording device 6 comprises a first communication interface for communicating with the OBP measuring device 1. The first communication interface is for example a wireless communication interface comprising an antenna 63 that is advantageously placed near the measuring device 1 when the measuring device 1 is worn by a user. The antenna 63 is for example integrated into eyeglasses, not represented on the figure, and/or into a for example disposable, flexible and hypoallergenic patch, also not represented on the figure, which are or is worn by the user during the monitoring time periods. Other means are however possible within the frame of the invention for placing the antenna 63 at a suitable distance from the measuring device 1 when the latter is worn by a user.

The portable recording device 6 further comprises a second communication interface for communicating with the computing device 7.

According to embodiments of the invention, when monitoring the at least one OBP, a user wears the measuring device 1, for example by placing the support in the form of a contact lens on his or her eye just like any conventional contact lens or by having the device in an implantable form previously implanted in one of his or her eyes, and carries the portable recording device 6, for example in a pocket or by hanging it around his or her neck. The antenna 63 is placed as close as possible to the user's eye wearing the measuring device 1 in order to allow the establishment of a first communication channel 150, for example a wireless communication channel, between the measuring device 1 and the recording device 6. In case of wireless communication, the antenna 63 is preferably oriented in a plane as parallel as possible to the plane of the antenna of the measuring device 1 in order to allow for an efficient powering of the microcontroller and/or of the OBP sensor over the communication channel 150, which is for example a close distance inductive communication channel. The antenna 63 is for example integrated in eyeglasses and/or into a patch surrounding the eye, for example into a disposable, flexible and hypoallergenic patch, and/or in a cap, a hat or in another piece of clothing or accessory worn by the user. Preferably, the antenna 63 is centered with the antenna of the measuring device 1 when the measuring device 1 and the portable recording device 6 are both worn by the user. The diameter of the antenna 63 of the portable recording device 6 is preferably larger than the diameter of the measuring device 1. The shape of the antenna 63 of the portable recording device 6 is for example round, oval, rectangular, polygonal, or any other appropriate shape. The shape of the antenna 63 of the portable recording device 6 is preferably adapted to the shape of the device, for example the eyeglasses, the patch, the piece of garment, etc., to which it is attached.

According to embodiments, while monitoring the at least one OBP, the portable recording device 6 powers the measuring device 1 through the first communication channel 150 at for example regularly spaced time intervals and collects data sent by the microcontroller for example through the antenna of the measuring device 1.

Collected data for example comprises electrical signals from the sensor and/or a value of the at least one monitored OBP calculated by the microcontroller of the measuring device 1 on the basis for example of the sensor's electrical signals. In embodiments, the collected data is stored in internal memory of the portable recording device 6.

The at least one OBP is for example measured at a predetermined frequency.

At some moments in time, for example once a day, once a week or once a month, the user and/or a practitioner connects the portable recording device 6 to a computing device 7, for example to a computer, over a second communication channel 160, for example a wireless communication channel, for example a Bluetooth, Wi-Fi or any other appropriate wireless communication channel. The second communication channel 160 can however also be any appropriate wired communication channel. Once the portable recording device 6 is connected to the computing device 7, the data collected and stored in the internal memory of the portable recording device 6 is transferred over the second communication channel 160 to the computing device 7 for further analysis, for example monitoring ocular biomechanical properties (OBP) and/or detecting and/or diagnosing and/or surveying ophthalmic diseases.

In embodiments, at least part of the data analysis and/or of the corresponding decisions are performed automatically with the help of one or more computer programs running on the computing device 7 or on an external server to which the computer device sends at least part of the downloaded data, or through cloud computing. The detection, diagnosis, control, determination and/or adaptation is performed in particular by at least partly automatically analyzing the variations of the at least one OBP measured during the monitoring period. In embodiments, the measured variations over time are for example compared with typical variation schemes corresponding for example to that of a healthy or standard eye. Any significant difference between the measured scheme and the sample scheme is for example automatically detected and/or analyzed in order to possibly diagnose an ophthalmic disease or a progression thereof. The measured values of the monitored at least one OBP and/or the typical values of said at least one OBP for a healthy or standard eye are for example displayed as one or more curves in a two-dimensional graph with the value of the at least one OBP being represented on the vertical axis and time on the horizontal axis.

In order to achieve the present invention, the inventors have compiled data from 50 centers in 13 countries in which OBP recording was performed by means of a Contact Lens Sensor (CLS) as part of different prospective studies or registries, approved by qualified body in each center.

A user should undergo a 24-hour recording session with a wireless CLS that has been approved for clinical use, among others, in Europe, and the United States. The device is based on a novel approach in which ocular dimensional changes measured at the corneo-scleral junction are assumed to correspond to changes in IOV and IOP. A microprocessor embedded in the contact lens sends an output signal proportional to that of the contact lens-embedded strain gauge. Wireless power and data transfer are achieved using a patched peri-orbital antenna from which a cable is connected to a portable recorder. The device can record IOV changes for up to 24 hours and remains active during sleep. Three hundred data points are acquired during a 30-second measurement period, repeated every 5 minutes. The technology is described in more detail below.

Figure 4:
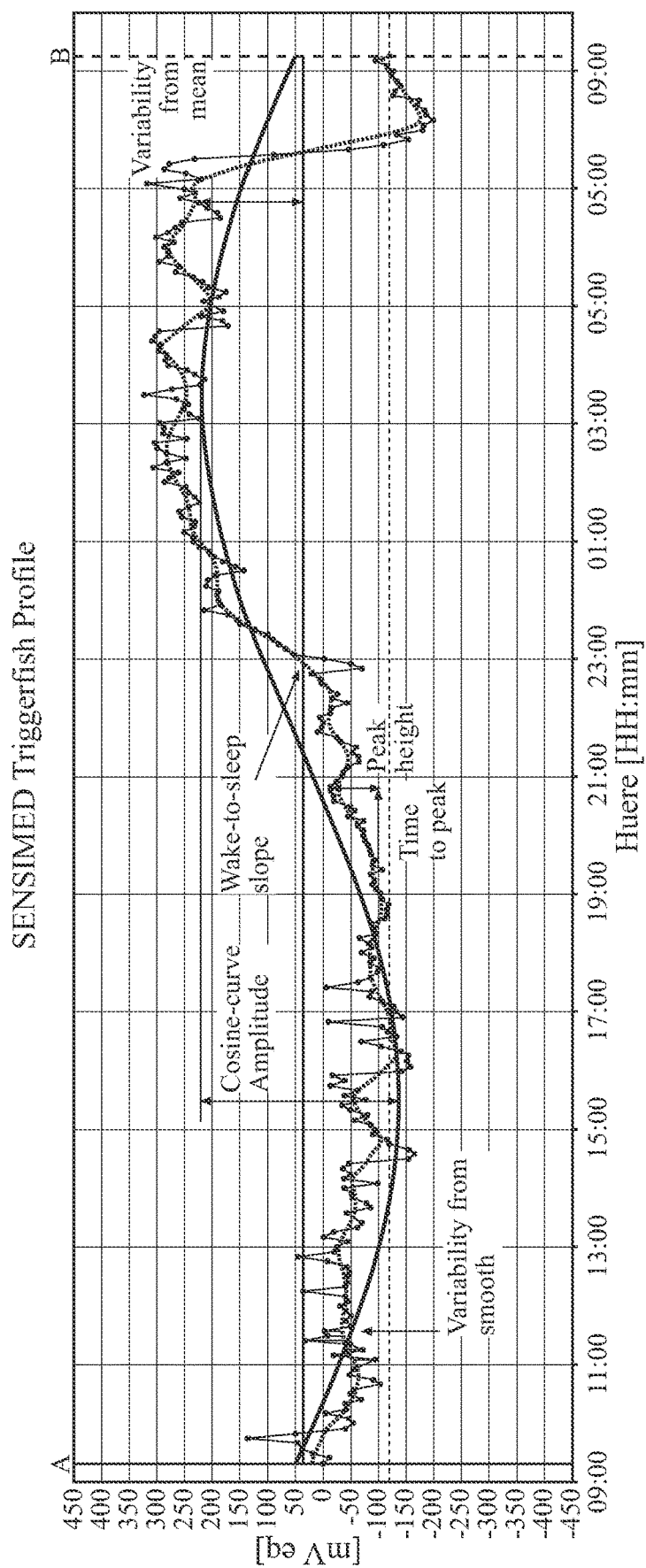
FIG. 4 illustrates an OBP time series plot representing the measured data then used according to the method of the present invention.

There are a large number of OBP parameters (N=55) that can be derived from the output of FIG. 4. These parameters are combined into 4 final OBP parameters obtained through linear combination of the initial 55 parameters.

Mean deviation (MD) slopes (in dB/year) are calculated with best linear unbiased prediction (BLUP) following mixed effects linear models testing the relationship between MD and time. Mixed effects models are more adequate than ordinary least squares models when analyzing longitudinal data points, such as repeated measurements of visual field test results, as they take into account the correlated nature of residuals. Then, one uses the relationship between each final parameter and the likelihood of being a fast progression using binary logistic models. The cut-off value of −1.0 dB/year is set to define fast progressors. The 4 final OBP parameters are tested in multivariable models including the following potential confounders: age at the time of CLS recording, visual field MD value closest to the date of recording, number of IOP-lowering medications, and surgery (laser and incisional) during the visual field testing period. Statistical analyses are performed using commercially available software (STATA, version 14; StataCorp LP, College Station, TX). Statistical significance is defined at $P<0.05$.

The hypothesis of the invention was that a combination of features derived from OBP parameters are associated with rates of visual field progression of treated glaucoma users. One found that a combination of OBP parameters obtained during a single 24-hour recording session has a significant ability to differentiate between users undergoing fast versus slow visual field progression, and that such ability is comparable to the predictive value of the current gold standard, that is, the average IOP measured with GAT over the entire follow-up period.

Among the 4 final OBP parameters, two were significantly associated with fast visual field progression even after taking into account potential confounders, such as age, treatment, and disease severity. The OBP parameters with highest loading were those related to nocturnal peaks and bursts for the first of these two parameters and those related to long peaks, wake-to-sleep slope, and the variation of the ocular pulse amplitude for the second of these two parameters. These findings suggest that OBP parameters correlated with IOP peaks during sleep, as well as IOP variation associated with systolic and diastolic blood pressure, may play a role in the pathogenesis of glaucoma progression.

Given the progressive and irreversible nature of glaucomatous damage, risk assessment plays an important role in clinical decision making. Users experiencing faster visual field progression are more likely to continue progressing at faster rates if no changes in treatment are made. One of the ways to estimate future visual field outcomes is by using pre-existing visual field data, as initial rates of change have a significant predictive ability over future slopes when one assumes linear trends. In fact, prior visual field progression rates can predict future visual field outcomes in users with glaucoma followed for a mean of 8 years. By using the rates of change of the first half of follow-up to predict the entire sequence of 10 or more visual field tests, one is able to predict the final visual field index (VFI) within ±10% of the estimated final VFI in 70% of users. Additionally, the VFI slopes of the first half and the entire sequence has a correlation coefficient of 0.84. Translating to the present invention, users deemed as fast progressions prior to OBP recordings are more likely to sustain faster progression in the future. Nonetheless, in clinical practice pre-existing rates of visual field change are not always available to estimate future outcomes. Therefore, our invention shows that 24-hour OBP recordings are significantly correlated with prior rates of progression and thus may be useful to assess the risk of future functional loss, even in situations when insufficient historical visual field information is available.

Furthermore, IOP is the only proven modifiable risk factor to prevent or slow glaucomatous visual field progression. As OBP patterns strongly correlate with IOP patterns, monitoring IOP variability with a 24-hour system provides more comprehensive assessment of IOP peaks and fluctuation that may be detrimental in glaucoma, and which are often overlooked with single measurements taken in office hours. In fact, the present invention shows that a single 24-hour session capturing circadian IOP-related rhythms provides similar information on rates of visual field progression as multiple IOP measurements with GAT over years of follow-up. Performing multiple 24-hour OBP recordings should show that the information provided is superior to that of multiple, longitudinal tonometric measurements.

Finally, one sees the association between the 24-hour OBP recordings and rates of visual field progression. It is remarkable that a single 24-hour recording with a device that measures volumetric changes associated with IOP is able to differentiate between eyes experiencing fast versus slow progression. In fact, this association is stronger than that seen when using the gold standard for IOP monitoring, i.e., the average follow-up IOP with GAT.

In conclusion, in a large diverse cohort of treated glaucoma users, a single 24-hour monitoring of IOP-related patterns provides a signature that significantly correlated with the rates of visual field progression. This signature performed better than the mean IOP during follow-up when discriminating between users experiencing fast versus slow progression. Future studies testing the predictive ability of this device are warranted.

In variant embodiments, the method and the system of the invention are used for monitoring the long-term evolution of at least one OBP, for example in order to evaluate the effectiveness of a medical treatment and/or in order to evaluate the mid- to long-term effects of a drug on the at least one OBP. Accordingly, the at least one OBP is measured continuously or at intervals during and/or after the medical treatment and/or drug application period. The values of the at least one OBP measured during the latest measuring period are compared, for example at least partly automatically compared, with previously measured values of the OBP, thereby allowing determining, for example at least partly automatically determining, a positive, negative or neutral evolution of the measured OBP over time, for example over days, weeks, months or years.

In applications of the present invention for the diagnosis and/or treatment of a user having an ophthalmic and/or a brain disease, for example, and/or in applications for the measurement of the effects of a substance and/or of an event on a measured OBP, several of the above described methods can be combined in order to obtain for example, but not exclusively, a more reliable diagnosis, a better follow up of a medical treatment and/or a more accurate knowledge of the effects of external elements on at least one OBP.

The above embodiments of the system and methods of the invention are illustrative and in no way limiting examples of the present invention. In particular, the invention is contemplated to encompass all variations of constructions, wherein a measuring device, a monitoring system and methods of measurements are used to measure the response of the eye to an eye blink stimulation, the pulsation of intraocular pressure and the rapid eye motion, etc. In embodiments, the system of the invention is configured for continuously and accurately monitoring one or more OBP, for example IOV and/or IOP and changes thereof, corneal curvature and/or micro-displacement of the eye, at a frequency of at least 10 Hz during an extended period of time, for example several hours. According to the invention, the monitoring system comprises computing means, for example a computer, having algorithms able to display, analyze and process the data measured during the monitoring periods and provide essential information on the ophthalmic condition of the eye and/or diagnose ophthalmic and/or brain diseases. Therefore, the principles and features of the present invention may be employed in various and numerous embodiments without departing from the scope of the invention. In particular, any combination of the above-described embodiments of the method is possible within the frame of the invention.

The invention claimed is:

1. Method for determining the likelihood of a user being at or beyond a certain rate and/or risk of visual field progression (VFP), comprising the following steps:
   a measuring step (S101) comprising measuring ocular biomechanical properties (OBP) through a continuous-wear sensor placed on or implanted in the eye, with said measurement comprising repeated data capture at regular time intervals;
   a recording step (S102) comprising recording the user's ocular biomechanical properties in the form of at least one OBP time series plot in a recorder;
   a processing step (S103) wherein at least one of a plurality of OBP parameters are extracted from the recorded OBP time series plot;
   a calculation step (S104) wherein the at least one of a plurality of OBP parameters are associated to VFP, and
   a determining step (S105) wherein one determines whether the visual field progression is at or beyond a certain VFP threshold and/or the probability that the said visual field progression is comprised within a specific range; wherein the extracted OBP parameters are at least one taken from the group comprising amplitude, minimum, maximum, standard-deviation, number of peaks, slopes, fitted cosinor curve of a 24-hour OBP profile, number of large peaks, mean peak ratio, amplitude of the cosine curve, wake-to-sleep slope, variability from the mean and area under the curve, or a combination thereof.

2. The method according to claim 1, wherein in the determining step (S105), the visual field progression threshold is 0 dB/year or less.

3. The method according to claim 1, wherein the processing step (S103) extracts a first number of first order parameters which are then combined to provide a second number, lower than the first number, of second order parameters.

4. The method according to claim 1, wherein the extracted OBP parameters are at least one taken from the group comprising amplitude, minimum, maximum, standard-deviation, number of peaks, slopes, fitted cosinor curve of a 24-hour OBP profile, mean peak ratio, amplitude of the cosine curve, wake-to-sleep slope, variability from the mean and area under the curve, or a combination thereof.

5. The method according to claim 1, wherein in the calculation (S104) step, the extracted OBP parameters are combined with additional user metadata.

6. The method according to claim 5, wherein the extracted OBP parameters and additional user metadata are combined through a logistic model.

7. The method according to claim 5, wherein the additional user metadata are taken from the group comprising latest TOP data, age, a number of medications taken during past 5 years, latest visual field mean defect.

8. The method according to claim 1, wherein the continuous-wear sensor is a wireless Contact Lens Sensor.

9. The method according to claim 8, wherein the continuous-wear sensor is implanted in the eye.

10. The method according to claim 1, further comprising an OBP data downloading step (S106) comprising transferring the OBP data from the recorder to a computer.

11. The method according to claim 10, wherein the downloading step consists in a wireless data transfer.

12. The method according to claim 1, further comprising a cleaning step (S107) prior to the processing step (S103) and adapted to clean the OBP time data by deleting the bad quality measured data.

13. The method according to claim 1, further comprising a result communicating step (S108) after the determining step (S105), adapted to send a signal to a receiver, said signal indicating the likelihood of being at or beyond a certain rate and/or risk of visual field progression.

14. The method according to claim 1, characterized in that it is a computer-implemented method.

15. The method according to claim 1, wherein the determining step (S105) determines the likelihood of being at or beyond a certain rate and/or risk of BNFL progression.

16. A system for predicting visual field progression in a user by carrying out the method of claim 1 the system comprising:

a continuous-wear sensor placed on or implanted in the eye adapted to measure ocular biomechanical properties with repeated data capture at regular time intervals;

a recorder adapted to record the user's ocular biomechanical properties in the form of at least one OBP time series plot, a processing unit for extracting at least one of a plurality of OBP parameters from the recorded OBP time series plot;

a calculation unit for associating the at least one of a plurality of OBP parameters to VFP, and a determining unit for determining whether the visual field progression is at or beyond a certain VFP threshold and/or the probability that the said visual field progression is comprised within a specific range.

* * * * *